US006946001B2

(12) United States Patent
Sanford et al.

(10) Patent No.: US 6,946,001 B2
(45) Date of Patent: Sep. 20, 2005

(54) MOBILE BEARING UNICOMPARTMENTAL KNEE

(75) Inventors: Adam Sanford, Warsaw, IN (US); Toby Farling, Warsaw, IN (US); Vincent Webster, Warsaw, IN (US); Robert Hodorek, Warsaw, IN (US); Scott Lazar, Cromwell, IN (US); Scott J. Steffensmeier, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/357,264

(22) Filed: Feb. 3, 2003

(65) Prior Publication Data

US 2004/0153164 A1 Aug. 5, 2004

(51) Int. Cl.[7] .................................................. A61F 2/38
(52) U.S. Cl. ................................... 623/20.33; 623/20.3
(58) Field of Search ......................... 623/20.29, 20.33, 623/20.3

(56) References Cited

U.S. PATENT DOCUMENTS

| 4,340,978 | A |   | 7/1982 | Buechel et al. |            |
|-----------|---|---|--------|----------------|------------|
| 4,711,639 | A | * | 12/1987| Grundei         | 623/20.33 |
| 5,282,868 | A | * | 2/1994 | Bahler          | 623/20.29 |
| 5,871,541 | A |   | 2/1999 | Gerber          |            |

FOREIGN PATENT DOCUMENTS

| EP | 0 519 872   | 12/1992 |
| FR | 2 778 332   | 11/1999 |
| WO | WO 95/14444 | 6/1995  |

* cited by examiner

Primary Examiner—Bruce E Snow
(74) Attorney, Agent, or Firm—Jonathan D. Feuchtwang; Zimmer Technology, Inc.

(57) ABSTRACT

An orthopedic knee component for implanting within a single compartment of a human knee includes, in a first embodiment a tibial tray having a superior surface having a plurality of tabs disposed along an exterior edge thereof, a bearing component having a superior surface adapted to articularly engage a femoral knee prosthesis and a circumferential groove disposed therearound with which the tabs of the tibial tray cooperatively engage such that the bearing component is movable relative to the tibial tray. In a second embodiment, an orthopedic knee component for implanting within a single compartment of a human knee includes: a tibial tray in supporting engagement with a bearing component, wherein the bearing component includes a superior surface adapted to articularly engage a femoral knee prosthesis and a pair of slots disposed along the superior surface of the bearing component, the femoral component having a pair of rails extending from the articulating surface thereof such that the rails can slidingly engage the slots, and such that the bearing component is movable relative to the tibial tray.

5 Claims, 4 Drawing Sheets

MOBILE BEARING UNICOMPARTMENTAL KNEE

BACKGROUND OF THE INVENTION

1. Field of the Invention

The present invention relates generally to prosthetic knee implants of the type commonly referred to as "mobile bearing." More specifically the invention relates to mobile bearing knees for use in unicompartmental ("uni") knee prostheses.

2. Description of the Related Art

Prosthetic knee implants having a bearing component that is movable relative to a fixed tibial tray during flexion and extension of a person's knee joint are known as mobile bearing knees and will be referred to as such throughout this document. Mobile bearing knees generally consist of a tibial tray affixed to a prepared proximal tibia and a bearing component which typically comprises ultra high molecular weight polyethylene ("UHMWPE"). The bearing component is adapted to allow a femoral component to articulate against the same. Often, there exists a mechanism or a plurality of mechanisms to restrict or limit movement of the bearing component relative to the tibial component during movement of the knee.

It has recently become a goal of physicians to perform orthopedic surgeries, such as knee arthroplasty, in a less invasive or minimally invasive manner. To this end, orthopedic surgeons have begun performing uni knee arthroplasty in situations where only one compartment of a patient's knee is affected by disease or trauma. Partial knee arthroplasty avoids causing trauma to the unaffected compartment of the knee. In addition, uni knee implants are smaller than total knee implants. Thus, partial knee arthroplasty is a naturally less invasive alternative to total knee arthroplasty. However, as uni prosthetic knee joints are less well known than their total knee replacement counterparts, few, if any, designs exist for mobile bearing uni knees.

SUMMARY OF THE INVENTION

The present invention, in one embodiment thereof, comprises an orthopedic knee component for implanting within a single compartment of a human knee having a tibial tray that includes a superior surface having a plurality of tabs disposed along an exterior edge thereof, a bearing component disposed upon the superior surface of the tibial tray having a superior surface adapted to articularly engage a femoral knee prosthesis and a circumferential groove disposed therearound with which the tabs of the tibial tray cooperatively engage such that the bearing component is movable relative to the tibial tray without tipping or leading to dislocation.

The invention, in a another embodiment thereof, comprises an orthopedic knee component for implanting within a single compartment of a human knee including a tibial tray in supporting engagement with a bearing component, wherein the bearing component includes a pair of slots disposed along the superior surface of the bearing component and a superior surface adapted to articularly engage a femoral knee prosthesis. The femoral component has a pair of rails extending from the articulating surface thereof, such that the rails can slidingly engage the slots and such that the bearing component is movable relative to the tibial tray.

An advantage of the present invention is that it provides a mobile bearing prosthetic knee useful in with a partial knee arthroplasty. Other advantages of the invention will be apparent to those of skill in the art upon reading the following descriptions and claim and upon viewing the appended drawings.

BRIEF DESCRIPTION OF THE DRAWINGS

The above-mentioned and other features and objects of this invention, and the manner of obtaining them, will become more apparent and the invention itself will be better understood by reference to the following description of an embodiment of the invention taken in conjunction with the accompanying drawings, wherein.

Figure 1:
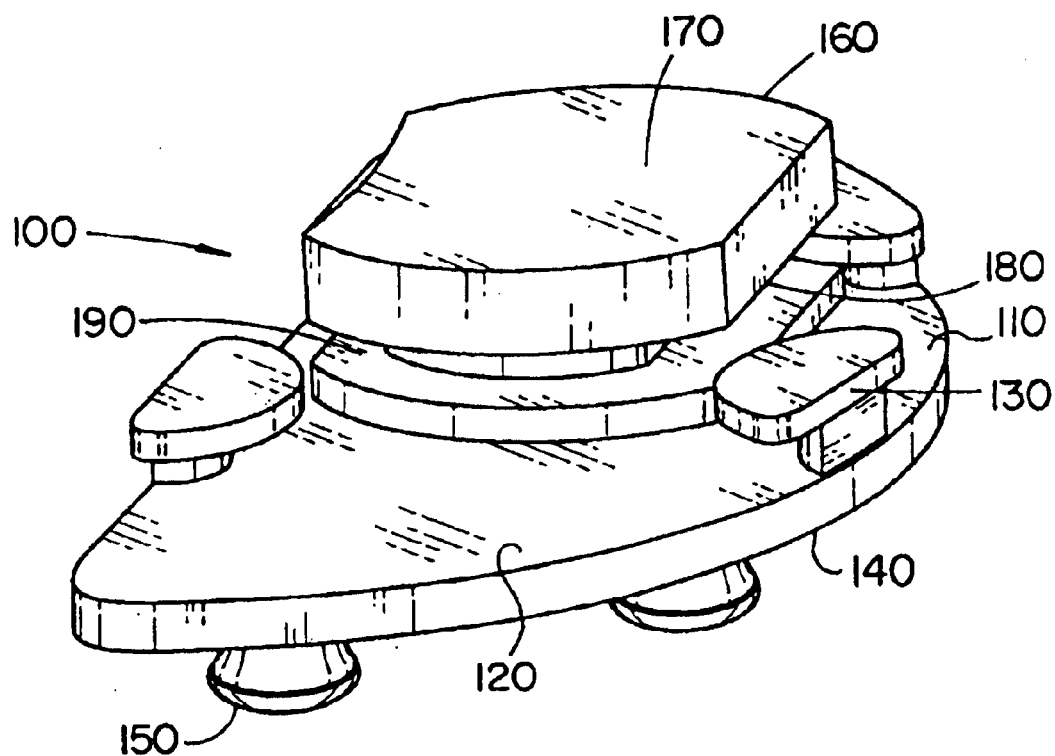
FIG. 1 is a perspective view of a first embodiment of the present invention
Figure 2:
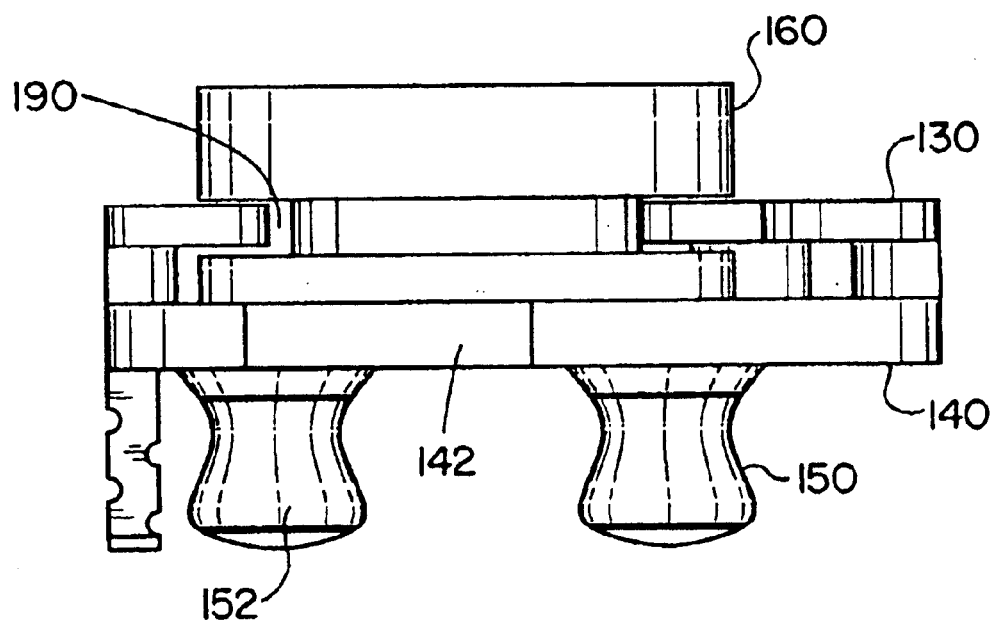
FIG. 2 is a side view of the first embodiment of the present invention

Corresponding reference characters indicate corresponding parts throughout the several views. Although the drawings represent an exemplary embodiment of the present invention, the drawings are not necessarily to scale and certain features may be exaggerated to better illustrate and explain the invention. The exemplification set out herein illustrates an exemplary embodiment of the invention only and such exemplification

DETAILED DESCRIPTION OF THE INVENTION

As used herein, the following directional definitions apply. Anterior and posterior mean nearer the front or nearer the back of the body respectively. Thus, for the knee joint described herein, anterior refers to that portion of the knee that is nearer the front of the body, when the leg is in an extended position. Proximal and distal mean nearer to or further from the root of the structure, respectively. For example, the distal femur is a part of the knee joint while the proximal femur is closer to the hip joint. Finally, the adjectives medial and lateral mean nearer the median plane or further from the median plane respectfully. The median plane is an imaginary vertical plane through the middle of the body that divides the body into right and left halves.

In FIG. 1, there is shown a perspective view of a prosthetic uni knee implant 100 according to a first embodiment of the present invention comprising: tibial tray 110 and bearing component 160. Implant 100 is insertable into the joint space within a single compartment of a human knee in order to replace bone and tissue lost to trauma or disease. It is to be appreciated that an embodiment of the present invention is useful for medial partial knee arthroplasty, lateral partial knee arthroplasty, or total knee arthroplasty.

Figure 3:
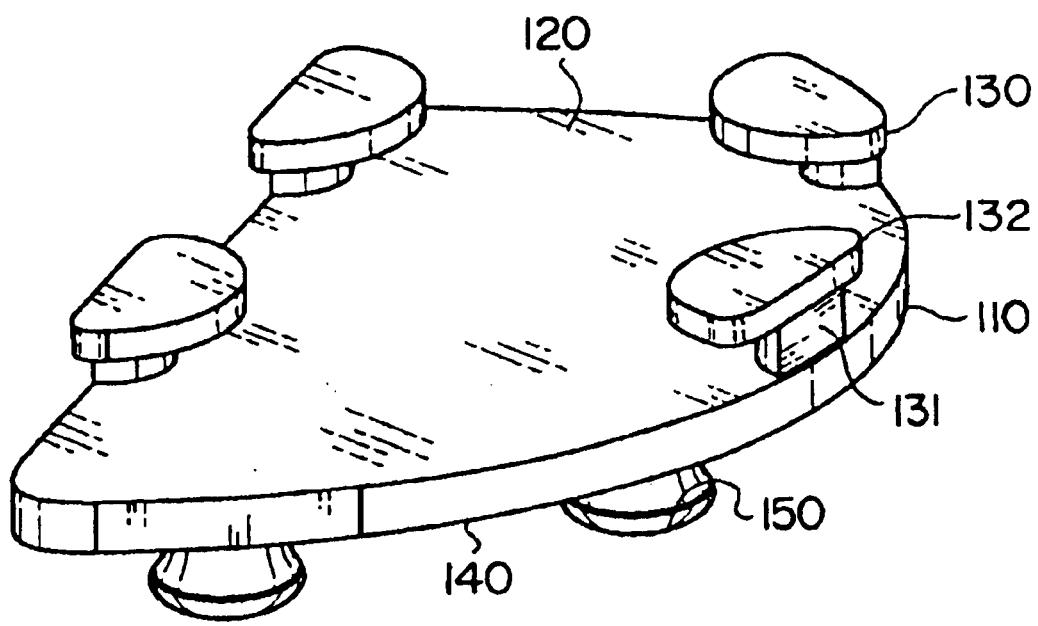
FIG. 3 is a perspective view of a tibial tray according to the first embodiment of the present invention.
Figure 3A:
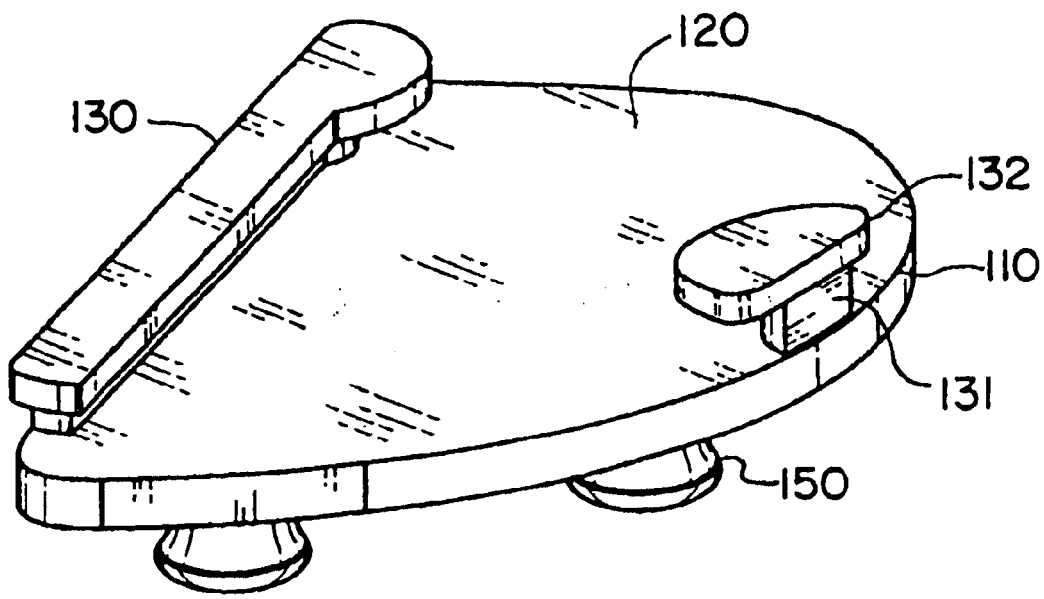
FIG. 3a shows an alternative embodiment of the tibial tray of FIG. 3.
Figure 4:
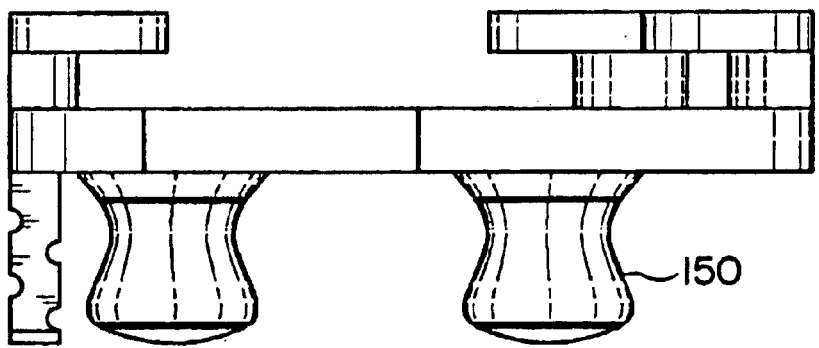
FIG. 4 is a side view of the tibial tray according to a first embodiment of the present invention.

Referring now to FIG. 3, tibial tray 110 of the present invention comprises: a superior surface 120, at least two tabs 130, and inferior surface 140, and pegs 150 for attaching tray 110 to a human tibia. Tibial tray 110 is appropriately sized to fit within the joint space created during a knee arthroplasty. Tibial tray 110 may further comprise any biocompatible material having the requisite mechanical properties necessary for tray 110 to function as a tibial implant, including metals, plastics, and ceramics. Generally, however, tibial tray 110 comprises a biocompatible metal such as titanium or cobalt alloy.

Referring again to FIG. 3, superior surface 120 is generally flat and smooth; it is adapted to allow bearing component 160 (described subsequently herein) to slidingly engage the same. Tibial tray 110 further comprises at least two tabs 130 disposed along the exterior edge of superior surface 120. Each tab 130 comprises a substantially "L" shape such that each tab comprises a first tab portion 131 connected to and extending superiorly from superior surface 120 of tray 110. Each tab 130 further comprises a second tab portion 132 that is connected to the free end of first tab portion 131 and that extends therefrom generally toward the interior of superior surface 120, such that second tab portion is generally parallel to superior surface 120.

Referring still to FIG. 3, Tibial tray 110 further comprises inferior surface 140. Inferior surface 140 comprises means 150 for fixedly attaching tibial tray 110 to a surgically prepared proximal tibia. Means 150 may comprise any means known in the art for attaching a tibial tray to a proximal tibia. However, the exact means 150 of attaching tibial tray 110 to a proximal femur are not important to the present invention. For example, means 150 may comprise pegs, screws, pins, a bone ingrowth surface, an elongated stem for insertion into the intramedullary canal of a tibia, or a combination of these features.

Referring back to FIG. 1, prosthetic knee implant 100 further comprises bearing component 160. Bearing component 160 generally comprises a thermoplastic or thermoset polymer material such as ultra high molecular weight polyethylene ("UHMWWPE") or highly cross-linked UHMWPE. Bearing component 160 further comprises a shape and size suitable for use as a bearing component in a uni prosthetic knee.

Bearing component 160 further comprises a superior surface 170 adapted to accommodate the rotational and translational articulation of a distal femur uni prosthesis. The exact shape of superior surface 170 or the exact design of such distal femoral implant, however, is not critical to this embodiment of the present invention.

Bearing component 160 also comprises inferior surface 180 shaped to slidingly engage superior surface 120 of tibial tray 110 such that bearing component 160 can move relative to tray 110. In the embodiment shown in FIGS. 1–4, surface 120 of tray 110 is flat, and bearing component 160 is movable in any direction in a plane that is generally parallel to surface 120.

Bearing component 160 further comprises a generally vertical circumferential wall having groove 190 disposed thereon. Groove 190 is has a depth and height suitable to allow any second tab portion 132 to fit therein. The depth and height of groove 190 are such that when second tab portion 132 of tabs 130 fit into groove 190 there is a gap remaining within the height of groove 190, such that bearing component 160 may easily slide along superior surface 120 of tibial tray 110. Tabs 130 prevent bearing component 160 from sliding off of superior surface 120 of tibial tray 110. It is desirable for at least one of tabs 130 to engage groove 190 in order to prevent bearing component 160 from tipping.

Figure 5:
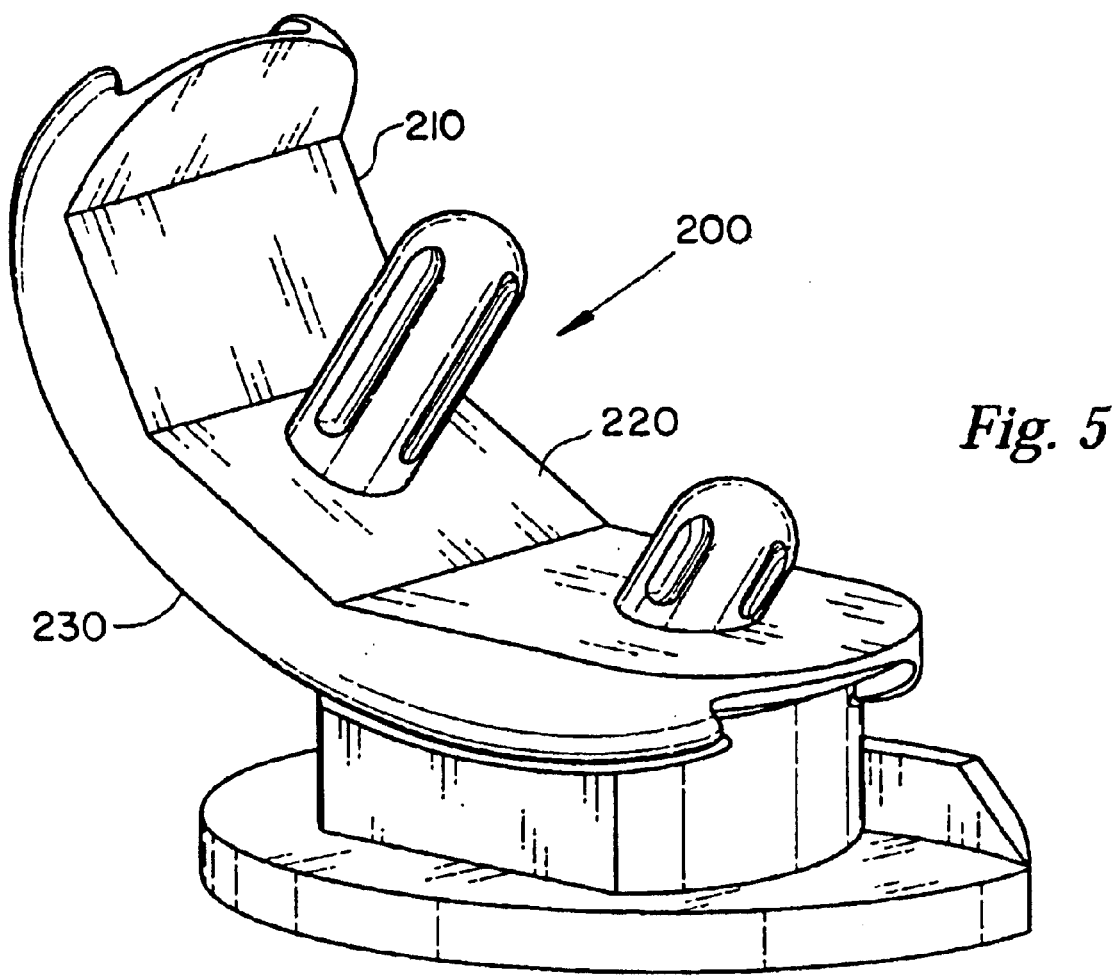
FIG. 5 is a perspective view of a second embodiment of the present invention.
Figure 7:
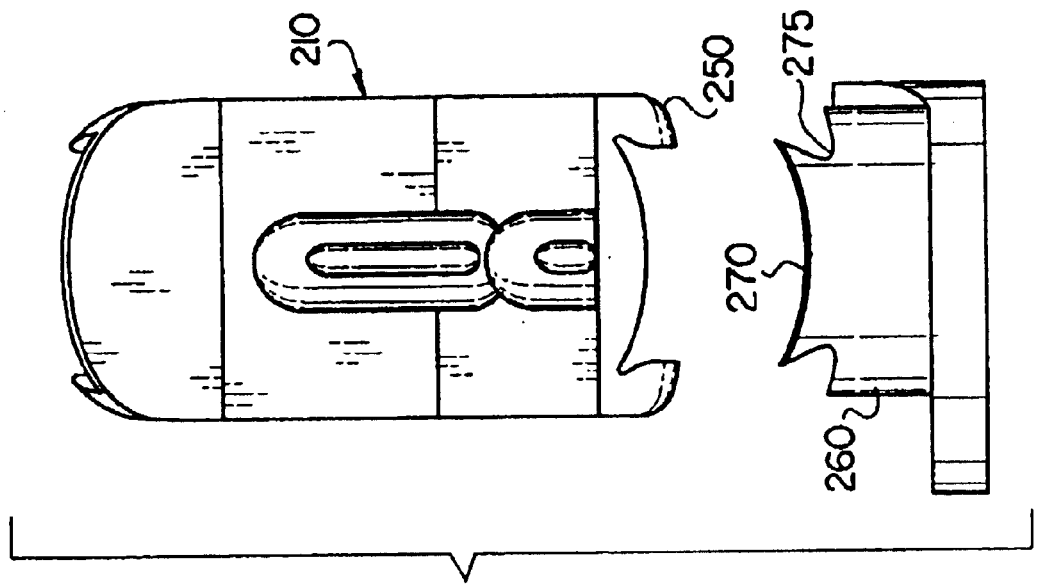
FIG. 7 is a front exploded view of the second embodiment of the present invention.
Figure 6:
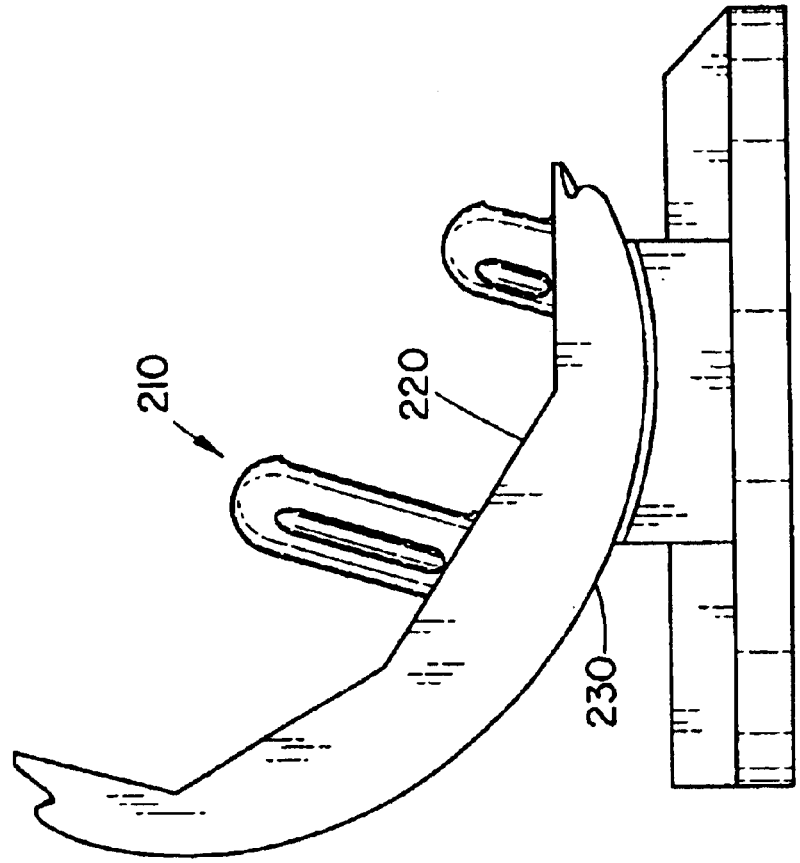
FIG. 6 is a side view of the second embodiment of the present invention.

FIGS. 5–7 show implant 200 according to a second embodiment of the present invention, wherein the implant comprises femoral component 210, bearing component 260 and tibial tray 290.

Referring now to FIG. 5, specifically femoral component 210 comprises a bone contacting surface 220 for engaging a surgically prepared distal femur. Bone contacting surface 220 generally includes a plurality of intersecting planes and means of affixing femoral component 210 to the prepared distal femur. These means may include press fitting, screws, bone ingrowth materials, posts or a combination of the same.

Referring now to FIGS. 5 and 6, femoral component 210 further comprises articulating surface 230 disposed opposite bone contacting surface 220. Articulating surface 230 is generally arcuated such that is can rotate and translate relative to a bearing component, such as the one described herein below.

Referring now to FIG. 7, femoral component 210 further comprises medial and lateral edges and a rail 250 disposed along each edge and extending from articulating surface 230. Rails 250 are adapted to slidingly engage slots 275 of bearing component 260 described below.

Continuing to refer to FIGS. 5 and 7, there is shown bearing component 260. Bearing component 260 comprises a shape and size suitable for use as a bearing component in a uni prosthetic knee.

Bearing component 260 further comprises a superior surface 270 adapted to accommodate the rotational and translational articulation of the femoral component. Slots 275, disposed along the medial and lateral edges of surface 270, are adapted to slidingly receive rails 250 or femoral component 210 such that femoral component 210 cannot move transversely relative to bearing component 260.

It is to be understood, however, that a variety of slot and rails configurations would be within the scope of the present invention. By way of example, but not limitation, the invention could comprise less than or more than two rail and slot combinations. Alternatively, the rails could be disposed on the superior surface 270 of bearing component 260 and the slots could be disposed on the articulating surface 230 of femoral component 210.

Bearing component 260 also comprises inferior surface 280 shaped to slidingly engage superior surface 291 of tibial tray 290 such that bearing component 280 can move relative to tray 290. In the embodiment shown in FIGS. 5–7, surface 291 of tray 290 is flat, and bearing component 260 is movable in any direction in a plane that is parallel to surface 291.

It will be appreciated by those skilled in the art that the foregoing is a description of a preferred embodiment of the present invention and that variations in design and construction may be made to the preferred embodiment without departing from the scope of the invention as defined by the appended claims.

We claim:

1. A mobile bearing unicondylar knee implant for implanting within a single compartment of a human knee joint and adapted to cooperate with a prosthetic femoral component, the implant comprising:

a bearing component, the bearing component having a superior surface adapted to allow articulation of the prosthetic femoral component thereon, an inferior surface adapted to slidingly engage a superior surface of a tibial tray, and an exterior wall having a groove disposed therearound; and a tibial tray having a superior surface having at least two tabs disposed along an edge thereof, the tabs having a first tab portion extending proximally from the superior surface of the tibial tray and a second tab portion attached to the first tab portion extending generally toward the center of the tibial tray such that the tabs are selectively engageable within the groove, wherein the bearing component freely moves in any direction in a plane that is generally parallel to said superior surface of said tibial tray while cooperation of said groove and said at least two tabs prevents said bearing component from sliding off the edge of said superior surface of said tibial tray.

2. The implant of claim 1, wherein the bearing component comprises a material selected from the group consisting of polyethylene, ultra high molecular weight polyethylene, and cross-linked ultra high molecular weight polyethylene.

3. The implant of claim 1, wherein the tibial tray further comprises an inferior surface having bone ingrowth means.

4. The implant of claim 3, wherein the inferior surface of the tibial tray comprises a material selected form the group consisting of porous titanium, porous tantalum.

5. The implant of claim 1, wherein the number of tabs is selected from the group consisting of 2 and 4.

* * * * *